United States Patent [19]

Dugger

[11] Patent Number: 5,036,155
[45] Date of Patent: Jul. 30, 1991

[54] PROCESS FOR ISOPROPYL 3S-AMINO-2R-HYDROXY-ALKANOATES

[75] Inventor: Robert W. Dugger, Mystic, Conn.

[73] Assignee: Pfizer Inc., New York, N.Y.

[21] Appl. No.: 560,940

[22] Filed: Jul. 31, 1990

Related U.S. Application Data

[60] Division of Ser. No. 374,200, Jun. 29, 1989, Pat. No. 4,965,372, which is a continuation-in-part of Ser. No. 299,863, Jan. 19, 1989, abandoned.

[51] Int. Cl.$^5$ ............... C07C 229/34; C07C 229/22; C07C 229/28
[52] U.S. Cl. .................. 560/39; 560/125; 560/170
[58] Field of Search ............ 560/39, 125, 170

[56] References Cited

U.S. PATENT DOCUMENTS

| | | | |
|---|---|---|---|
| 4,599,198 | 7/1986 | Hoover | 260/998.2 |
| 4,656,269 | 4/1987 | Iizuka et al. | 544/139 |
| 4,711,958 | 12/1987 | Iizuka et al. | 544/139 |
| 4,814,342 | 3/1989 | Hoover et al. | 514/385 |

OTHER PUBLICATIONS

Johnson, J. Med. Chem. 25, 605–610 (1982).
Rich et al., J. Org. Chem. 45, 2288–2290 (1980).
Tobe et al., Agric. Biol. Chem. 43, 591–596 (1979).
Nishizawa et al., J. Med. Chem. 20, 510–515 (1977).
Miller et al., J. Org. Chem. 47, 4928–4933 (1982).
Seebach et al., Helv. Chim. Acta. 63, 197–200 (1980).
Seebach et al., Organic Synthesis 63, 109–120 (1984).
Gao et al., J. Am. Chem. Soc. 110, 7538–7539 (1988).
Rabin et al., Biochemistry 7, 377–388 (1968).
Chemical Abstracts 68:36934a.

*Primary Examiner*—Bernard Dentz
*Attorney, Agent, or Firm*—Peter C. Richardson; J. Trevor Lumb; Robert K. Blackwood

[57] ABSTRACT

Process and intermediates for isopropyl 3S-amino-4-cyclohexyl-2R-hydroxybutyrate and 3S-amino-2R-hydroxy-5-methylhexanoate from R-malic acid. These products are of known utility in the synthesis of certain renin inhibitors.

6 Claims, No Drawings

PROCESS FOR ISOPROPYL 3S-AMINO-2R-HYDROXY-ALKANOATES

CROSS-REFERENCE TO RELATED APPLICATION

This application is a division of co-pending application Ser. No. 07/374,200, filed June 29, 1989, now U.S. Pat. No. 4,965,372 which is a continuation-in-part of application Ser. No. 07/299,863, filed Jan. 19, 1989 now abandoned.

BACKGROUND OF THE INVENTION

The present invention is directed to compounds defined by the formula (X) below, including isopropyl 3S-amino-2R-hydroxy-4-phenylbutyrate which is also specifically depicted by the formula (I) below when R is $C_6H_5$. The latter is converted by a conventional hydrogenation process to isopropyl 3S-amino-4-cyclohexyl-2R-hydroxybutyrate (of the formula (I) below when R is cyclohexyl). The present invention is also directed to various steps of the multistep process used in the preparation of the compounds of the formula (I) from R-malic acid. The compounds of the formula (I) when R is $(CH_3)_2CH$ or cyclohexyl are of known utility in the synthesis of various renin inhibiting compounds (see, for example, Johnson, J. Med. Chem., vol. 25, pp. 605–610, 1982; Rich et al., J. Org. Chem., vol. 45, pp. 2288–2290, 1980; Tobe et al., Agric. Biol. Chem., vol. 43, pp. 591–596, 1979; Nishizawa et al., J. Med. Chem., vol. 20, pp. 510–515, 1977; Iizuka et al., U.S. Pat. No. 4,711,958; and Hoover et al., EP published patent application No. 266,950).

Heretofore, 3S-amino-4-cyclohexyl-2R-hydroxybutyrate and 3S-amino-2R-hydroxy-5-methylhexanoate have been prepared by multistep, low yield syntheses from L-phenylalanine and L-leucine, respectively, involving wasteful co-production of extensive amounts of undesired 2S,3S-diastereoisomers, and the use of highly toxic cyanohydrin processes (Iizuka et al., loc. cit.; Rich et al., loc. cit.; Hoover et al., loc. cit.; Hoover, U.S. Pat. No. 4,599,198; Nashizawa et al., loc cit). In marked contrast, the present route, which begins with readily available L-malic acid (i.e., (R)-malic acid), is highly stereoselective, avoids the use of cyanohydrins and produces relatively high yields of the desired products.

The diethyl ester of present 2R-hydroxy-3S-(phenylmethyl)butanedioic acid, of the formula (II) below when R is $C_6H_5$, was previously prepared from (R)-malic acid via alkylation of diethyl (R)-malate (Seebach et al., Helv. Chim. Acta, vol. 63, pp. 197–200, 1980; cf. also Seebach et al., Org. Synth., vol. 63, pp. 109–120, 1984). Present use of the diisopropyl ester unexpectedly leads to higher overall yields while maintaining substantially the same stereoselectivity (i.e., about a 10:1 ratio of desired 2R,3S: undesired 2R,3R-diastereomer).

Since the completion of this invention, Gao and Sharpless [based on the text of J. Am. Chem. Soc., vol. 110, pp. 7378-9 (Nov., 1988), not the evidently erroneous stereodiagrams] appear to have described the synthesis of diisopropyl 2R-hydroxy-3S-(phenylmethyl)butandioate, of the formula (IX) below, from (+)-diisopropyl 2R,3R-tartrate.

SUMMARY OF THE INVENTION

The present invention is specifically directed to a step-wise process for the preparation of an isopropyl 3S-amino-2R-hydroxyalkanoate of the formula

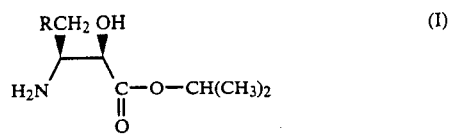

wherein R is cyclohexyl, phenyl or isopropyl, which comprises the steps of (a) reacting a 2R,3S-malic acid derivative of the formula

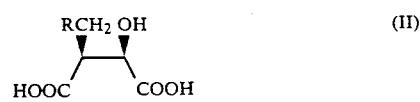

with excess of an acid chloride of the formula $R^1COCl$ or an anhydride of the formula $(R^1CO)_2O$, wherein $R^1$ is $(C_1-C_4)$alkyl or phenyl, to form a cyclic anhydride of the formula

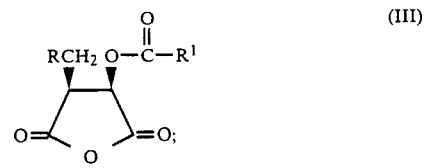

(b) reacting said cyclic anhydride of the formula (III) with excess of isopropanol to form a hemiester of the formula

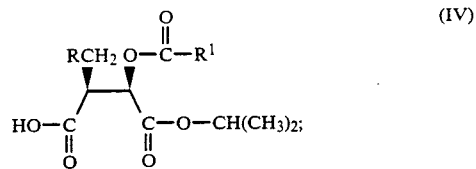

(c) activating the carboxylic acid group of said hemiester of the formula (IV), preferably as a mixed anhydride of the formula

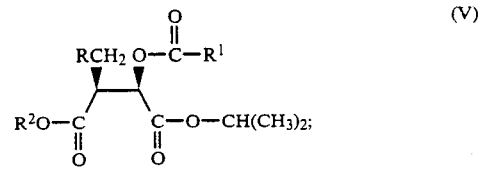

wherein $R^2$ is $(C_2-C_4)$alkoxycarbonyl, phenoxycarbonyl or benzyloxycarbonyl; and reacting the resulting activated form of the acid with $NH_3$ to form an esteramide of the formula

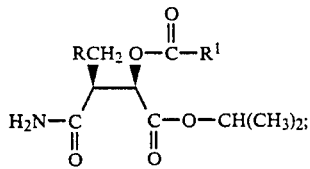

(VI)

(d) rearranging said ester-amide of the formula (VI) by the action of Pb(OCOCH₃)₄ in t-butanol to form a t-butyloxycarbonylamino ester of the formula

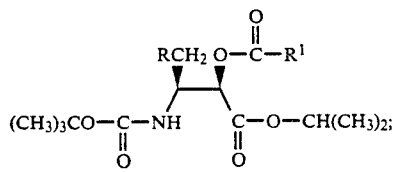

(VII)

and (e) solvolizing said t-butyloxycarbonylamino ester of the formula (VII) with isopropanol in the presence of an acid catalyst to form said isopropyl 3S-amino-2R-hydroxyalkanoate of the formula (I).

The preferred value of $R^1$ is methyl, and the preferred value of $R^2$, when the acid group of (IV) is activated as mixed anhydride, is ethoxycarbonyl.

When R is phenyl, the present invention further comprises hydrogenation of said isopropyl 3S-amino-2R-hydroxy-4-phenylbutyrate of the formula (I) wherein R is phenyl over a rhodium catalyst to form isopropyl 3S-amino-4-cyclohexyl-2R-hydroxybutyrate of the formula (I) wherein R is cyclohexyl.

Additionally, the present invention further comprises preparation of said 2R,3S-malic acid derivatives of the formula (II) by the sequential steps of (i) esterifying R-malic acid with excess isopropanol in the presence of an acid catalyst to form diisopropyl R-malate;

(ii) converting said diisopropyl malate to the enolic carbanion by the action of a strong base; when R is phenyl, (iii) reacting said carbanion with a benzylating agent to form diisopropyl 2R-hydroxy-3S-(phenylmethyl)butanedioate of the formula (IX) wherein R is phenyl; or

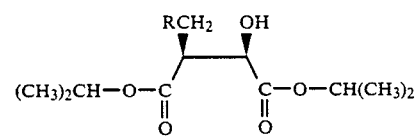

(IX)

when R is isopropyl, (iii) reacting said enolate with a methallylating agent to form diisopropyl 2R-hydroxy-3S-(2-methyl-2-propenyl)butanedioate, followed by hydrogenation to produce diisopropyl 2R-hydroxy-3S-(isobutyl)butanedioate of the formula (IX) wherein R is (CH₃)₂CH; and (iv) hydrolyzing said butanedioate ester in the presence of water and a basic catalyst to form said 2R-hydroxy-3S-(phenylmethyl or isobutyl)butanedioic acid of the formula (II); or when R is cyclohexyl, (v) hydrogenating the compound of the formula (II) wherein R is phenyl over a Rh catalyst to form a compound of the formula (II) wherein R is cyclohexyl.

Finally, the present invention is directed to certain of the above compounds of the formulas (I)–(VII) which are alternatively depicted by the single formula

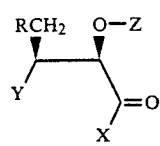

(X)

wherein

R is cyclohexyl, phenyl or isopropyl; and in a first alternative,

Z is

$R^1$ is (C₁-C₄)alkyl or phenyl; and
X and Y are taken together and are

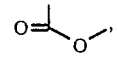

forming a cyclic anhydride; or
X and Y are taken separately, X is —O—CH(CH₃)₂ and Y is HO—C—, R²O—C—, H₂N—C— or
       ‖        ‖        ‖
       O        O        O (CH₃)₃CO—C—NH—; where
         ‖
         O $R^2$ is (C₂-C₄)alkoxycarbonyl, phenoxycarbonyl or benzyloxycarbonyl; or, in a second alternative, Z is hydrogen; and
X is —OH and Y is HO—C—; or
  ‖
  O X is —O—CH(CH₃)₂ and Y is (CH₃)₂CH—O—C— or NH₂,
           ‖
           O with the proviso that when Y is NH₂, R is C₆H₅.

As used herein, the expression "reaction-inert solvent" refers to a solvent which does not interact with starting materials, reagents, intermediates or products in a manner which adversely affects the yield of the desired product. Under the conventional types of nomenclature used herein, "butyric/butyrate" and "butanoic/butanoate" are used interchangably.

DETAILED DESCRIPTION OF THE INVENTION

The various process steps of the present invention are readily carried out in the following sequence, referring to the formulas enumerated and depicted above:

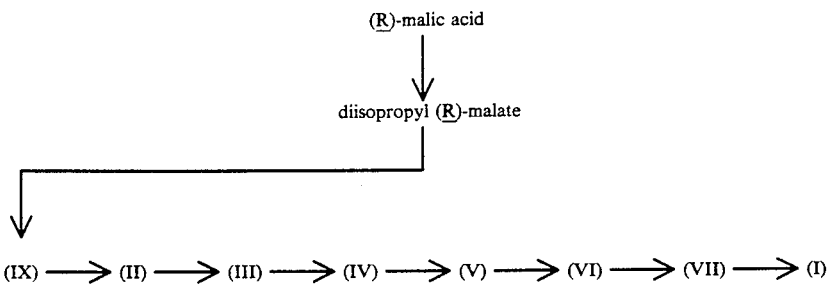

(IX) $\longrightarrow$ (II) $\longrightarrow$ (III) $\longrightarrow$ (IV) $\longrightarrow$ (V) $\longrightarrow$ (VI) $\longrightarrow$ (VII) $\longrightarrow$ (I)

Thus, in the initial step, commercially R-malic acid is converted to its diisopropyl ester by conventional means, e.g., by reaction of the diacid in excess isopropanol in the presence of a strong, preferably anhydrous or near anhydrous, acid catalyst such as dry HCl (as exemplified below), $H_2SO_4$ or p-toluenesulfonic acid, or in the presence of sulfonyl chloride (which in catalytic quantities will initially form ester via acid chloride and/or cyclic anhydride but, in coproducing HCl, ultimately functions in the same way as an acid catalyst). When dry HCl is used as catalyst, a solution of the malic acid in isopropanol is generally saturated with dry HCl at or below room temperature, with later heating (e.g., at the reflux temperature of the isopropanol solvent) to achieve complete esterification. Dry HCl is the catalyst of choice, since there is no evident racemization during the esterification process.

Stereoselective 3S-alkylation of the resulting diisopropyl R-malate is achieved by first irreversibly converting the malate ester to the anion. The basic reagent preferred for this purpose is lithium diisopropylimide, generally formed in situ in a polar ether such as tetrahydrofuran from molar equivalent amounts of diisopropylamine and butyllithium (in hexane) at low temperature, e.g., $-50°$ to $-90°$ C., conveniently at about $-78°$ C., the temperature achieved with an acetone-dry ice bath. Once complete conversion is achieved (after 0.5-1 hour at about $-78°$ C.), no more than half a molar equivalent of the malate ester is added, conveniently at the same low temperature. However, to assure maximal formation of the required enolate, the temperature is raised, e.g., to about $-20°$ to $-10°$ for about 1 hour. Alkylation is then achieved by then adding an alkylating agent (conveniently, benzyl bromide or methallyl chloride, one mole/mole of the malate ester, optionally in the presence of sodium iodide) and allowing the reaction mixture to warm to higher temperatures (e.g., $15°-35°$ C., conveniently ambient temperature) and proceed substantially to completion. For example, the reaction is greater than 95% complete after 18 hours at $20°-25°$ C. at an initial concentration which is about 0.5M in both the enolate and benzyl bromide. When the product is the isopropenyl derivative, it is conventionally hydrogenated to the corresponding isopropyl derivative. The preferred catalyst is Wilkinson catalyst, $(Ph_3P)_3RhCl$, under mild conditions (e.g., 30 psig and room temperature) in a reaction-inert solvent such as methanol.

The resulting diisopropyl 2R-hydroxy-3S-(phenylmethyl or isobutyl)butanedioate, of the above formula (IX), is then conventionally hydrolyzed with aqueous base to form the desired 2R-hydroxy-3S-(phenylmethyl or isobutyl)butanedioic acid of the formula (II) above. Aqueous NaOH, in the presence of a water-miscible reaction inert solvent such as tetrahydrofuran to solubilize the diester at a temperature in the range of $20°-50°$ C., as exemplified below, are particularly well-suited conditions.

Alternatively, when R is isopropyl, the precursor diisopropyl 3-(2-methyl-2-propenyl) ester is first hydrolyzed to the corresponding diacid and then hydrogenated to form the desired compound of the formula (II) wherein R is $(CH_3)_2CH$. Hydrolysis and hydrogenation conditions remain as detailed in the immediately preceding paragraphs.

The compound of the formula (II) wherein R is cyclohexyl is obtained by hydrogenation of the compound of the formula (II) wherein R is phenyl over a heterogeneous rhodium catalyst such as $Rh/Al_2O_3$, generally in a reaction-inert solvent such as methanol. Temperature and pressure are not critical. Conveniently hydrogenation is accomplished at ambient pressures less than 100 psig, thus avoiding cost of heating or cooling and the need for expensive high pressure hydrogenation equipment.

In the next stage the 2R-hydroxy-3S-butanedioic acid derivative (II) is concurrently acylated and cyclized to the cyclic anhydride thus forming a compound of the formula (III). This conversion is readily done by reacting the acid (II) with excess of a $(C_2-C_5)$alkanoyl chloride or anhydride, or benzoyl chloride or anhydride. The preferred value of R' is methyl and the preferred reagent is acetyl chloride. Temperature is not critical, with temperatures in the range of 10° C. to 50° C. being generally satisfactory. When acetyl chloride is the reagent, ambient temperature is well-suited, thus avoiding the cost of warming or cooling the reaction mixture. In isolating the product by simply stripping away excess acid chloride/anhydride and coproduced acid (HCl and/or RCOOH), it is important that all HCl and/or excess RCOCl be thoroughly stripped away, since residual HCl (or HCl formed from residual RCOCl) will catalyze esterification of the other carboxy group with isopropanol in the next step.

With a resulting high degree of the desired regioselectivity, the acylated cyclic anhydride (III) is then reacted with isopropyl alcohol to provide the ester-acid of the formula (IV). This reaction is readily accomplished in excess isopropyl alcohol at a temperature in the range of 0°-60°, conveniently at ambient temperature.

The acid group of acid-ester is then conventionally activated, e.g., as the acid chloride or preferably as the mixed anhydride, of the formula (V) above. Typically, the acid group is activated by formation of the mixed anhydride by reaction of ethyl chloroformate in the presence of triethylamine at about 0°-5° C. in a reaction-inert solvent such as tetrahydrofuran. Generally without isolation, the activated form of the acid is reacted with excess ammonia (conveniently in the form of concentrated ammonium hydroxide) to form the esteramide of the formula (VI) above. For example this reaction is readily accomplished by simply adding excess concentrated NH₄OH to a cold solution of mixed anhydride and allowing the reaction to proceed to completion at 0°–5° C. Alternatively, the mixed anhydride (V) wherein $R^2$ is ethoxycarbonyl is formed by the interaction of the acid of the formula (IV) with N-ethoxycarbonyl-2-ethoxy-1,2-dihydroquinoline (EEDQ) in a reaction inert solvent such as acetonitrile, which in this case is conveniently reacted with ammonium bicarbonate to form the desired ester-amide of the formula (VI).

In the next step, the ester-amide (VI) is rearranged to yield the t-butyloxycarbonylamino ester of the above formula (VII), readily accomplished by the action of 1-1.1 molar equivalents of lead tetracetate in excess t-butanol as both reactant and solvent. This reaction is usually carried out at elevated temperature (e.g. at about 65°–100° C.), conveniently at the reflux temperature of the reaction mixture (about 80°–85° C.).

The resulting compound of the formula (VII) is then converted to the isopropyl 3S-amino-2R-hydroxyalkanoate of the above formula (I). This selective "hydrolysis" is readily accomplished by acid catalyzed solvolysis, conveniently using dry HCl or $CH_3SO_3H$ in excess isopropyl alcohol at a temperature in the range of ambient to 100° C., preferably at about 80°–85° C., the reflux temperature of the reaction mixture, in order to achieve complete solvolysis within a reasonable period of time without use of a pressurized container.

Finally, when the product of the formula (I) is isopropyl 3S-amino-2R-hydroxy-4-phenylbutanoate, it is hydrogenated to form the required 3S-amino-4-cyclohexyl-2R-hydroxybutyrate of the formula (I) wherein R is cyclohexyl. This hydrogenation is conveniently accomplished using a heterogeneous rhodium catalyst (e.g. Rh/C), generally in a reaction inert solvent such as isopropanol. Temperature and pressure are not critical. As above, hydrogenation is conveniently accomplished at ambient temperature, and at pressures less than 100 psig.

Isopropyl 3S-amino-4-cyclohexyl-2R-hydroxybutyrate and 3S-amino-2R-hydroxy-5-methylhexanoate are used as intermediates in the further synthesis of renin inhibitors, for example, according to references cited above.

The present invention is illustrated by the following examples. However, it should be understood that the invention is not limited to the specific details of these examples. All ¹H-NMR data were obtained on a Varian XL-300 with $CDCl_3$ as the solvent unless otherwise indicated. Rotations were generally obtained on chromatographed or recrystallized material. Concerning abbreviations: MeOH=methanol; i-PrOH=isopropanol; EtOAc=ethyl acetate; THF=tetrahydrofuran; DMSO=dimethylsulfoxide; t-BuOH=t-butanol; and Pb(OAc)₄=lead tetracetate.

EXAMPLE 1

Diisopropyl (R)-Malate (R)-Malic acid (26.8 g, 0.20 mol) was dissolved in 300 ml of i-PrOH. The solution was cooled in an ice bath and HCl bubbled into the solution until approximately 15 g of HCl had been absorbed. The reaction mixture was refluxed for 7 hours, then (as a matter of convenience) stirred at room temperature for 16 hours. i-PrOH was removed under vacuum in a rotating evaporator. The residue was dissolved in 250 ml of EtOAc and washed with saturated NaHCO₃ (2×50 ml). The ethyl acetate layer was dried with Na₂SO₄, filtered and the volatiles removed under vacuum yielding 37.9 g of a clear, colorless liquid. The latter was distilled (0.025 mm, bp 82°–85° C.) giving 34.2 g of title product as a clear, colorless liquid (78% yield). ¹H-NMR delta 1.197 (3H, d, J=6.3), 1.202 (3H, d, J=6.3), 1.227 (3H, d, J=6.3), 1.233 (3H, d, J=6.3), 2.73 (2H, ABX, J=5.1, 5.1, 18.0), 3.21 (1H, d, J=5.2, —OH), 4.38 (1H, q, J=5.1), 5.00 (1H, septet, J=6.3), 5.08 (1H, septet, J=6.3). $R_f$=0.36 (25% EtOAc/hexanes) [alpha]$_D$= +12.1° (c=2.6, MeOH). This ester has been previously disclosed, without details or characterizing physical properties, by Miller et al., J. Org. Chem., v. 47, pp. 4928–4933, 1982.

EXAMPLE 2

Diisopropyl 2R-Hydroxy-3S-(phenylmethyl)butanedioate

To 51.1 g (70.7 ml, 0.505 mol) of diisopropyl amine in 200 ml of THF at −78° C. was added 50.5 ml (0.505 moles) of 10M butyl lithium (in hexanes) and stirred at −78° C. for 45 minutes. Then a solution of 50 g (0.229 moles) of the title product of the preceding Example in 50 ml of THF was added dropwise over a 30 minute period. The reaction mixture was allowed to warm to −15° C. and held at that temperature for 1 hour. Benzyl bromide (39.2 g, 0.229 moles) was added, the reaction stirred at −15° C. for 15 minutes, then allowed to warm to room temperature and stir for 18 hours. Water was added (500 ml) and the mixture was extracted with EtOAc (3×300 ml). The combined EtOAc extracts were washed with 100 ml of 5% HCl and 100 ml of 5% NaOH, and then dried over Na₂SO₄. After filtration and removal of the solvents under vacuum, present title product was obtained as an orange oil was (63 g). ¹H-NMR delta 1.15 (3H, d, J=6), 1.19 (3H, d, J=6), 1.23 (3H, d, J=6), 1.26 (3H, d, J=6), 2.93 (1H, dd, J=5,12), 3.06-3.21 (2H, m), 3.26 (1H, d, J=7, —OH), 4.03 (1H, dd, J=3,7, 4.98 (1H, septet, J=6), 5.06 (1H, septet, J=6), 7.1-7.4 (5H, m). The minor diastereomer can be observed at delta 4.09 in approximately a 10:1 ratio. IR (neat) 3500, 2980, 1720 $cm^{-1}$. [alpha]$_D$= −11.9° (c=1.0, CHCl₃). $R_f$=0.50 (25% EtOAc/hexanes). HRMS Calc. for $C_{17}H_{24}O_5$:308.1617. Observed: 308.1624.

EXAMPLE 3

2R-Hydroxy-3S-(phenylmethyl)butanedioic Acid (II, R=C₆H₅)

The entire product of the preceding Example was dissolved in 200 ml of THF. 71.9 ml of 15M NaOH was added followed by 50 ml of water. The temperature of the reaction mixture rose to approximately 45° C. The mixture was stirred vigorously for 18 hours, then diluted with water (400 ml) and washed with 200 ml of EtOAc to remove any neutral impurities. The aqueous solution was acidified to pH 1 with 6N HCl and extracted with EtOAc (3×200 ml). The combined EtOAc extracts were dxried with Na₂SO₄, filtered, evaporated on a rotating evaporator to yield 41.8 of an orange oil (approx. an 80% crude yield overall from diisopropyl (R)-malate). The oil was dissolved in a minimum amount of hot CHCl₃ and allowed to cool slowly to room temperature, then cooled in an ice bath, and a first crop of title product recovered by filtration. The filtrate was reduced in volume and recooled to yield a second crop to yield a total of 16.7 g of present title product as a white solid, mp 138°-138.5° C. $^1$H-NMR delta 2.78 (1H, m), 2.95 (2H, m), 3.98 (1H, d, J=5), 7.25 (5H, m). The minor diastereromer appears in the crude product as delta 4.4 (1H, d, J=5). IR (DMSO) 3250-2600, 1720 cm$^{-1}$. [Alpha]$_D$= +2.9° (c=5.0, H$_2$O). HRMS Calc. for C$_{11}$H$_{12}$O$_5$:224.0681. Observed: 224.0865.

EXAMPLE 4

2R-Acetoxy-3S-(phenylmethyl)butanedioic Anhydride (III; R=C$_6$H$_5$, R$^1$=CH$_3$)

To 80 ml (72.7 g, 0.93 mol) of acetyl chloride was added 38.4 g of the title product of the preceding Example. The reaction mixture was stirred at room temperature for 6 hours. The excess acetyl chloride and co-produced acetic acid were removed by distillation, first at 1 atm and then under vacuum to produce present title product in substantially quantitative yield. $^1$H-NMR delta 2.07 (3H, s), 2.98 (1H, dd, J=8,16), 3.14 (1H, 5,16), 3.66 (1H, m), 5.78 (1H, d, J=8), 7.2 (5H, m).

EXAMPLE 5

Isopropyl 2R-Acetoxy-3S-carboxy-4phenylbutanoate (IV, R=C$_6$H$_5$, R$^1$=CH$_3$)

To the entire product of the preceding Example was added 100 ml of i-PrOH, and the mixture stirred at room temperature for 3 hours. The excess i-PrOH was removed under vacuum. The last traces of i-PrOH were removed by azeotroping with toluene to yield present title product as 35.2 g of a clear, colorless liquid (67% overall from the title product of Example 3). $^1$H-NMR delta 1.18 (3H, d, J=6), 1.20 (3H, d, J=6H), 2.14 (3H, s), 2.79 (1H, dd, J=7,14), 3.14 (1H, dd, J=7,14), 3.34 (1H, m), 5.01 (1H, septet, J=6), 5.10 (1H, d, J=4), 7.2 (5H, m). IR (neat) 3300-2600, 1760-1700. [alpha]= +9.1° (c=1.5, CHCl$_3$). R$_f$=0.60 (75% EtOAc/hexanes). HRMS Calc. for C$_{16}$H$_{20}$O$_6$:308.1254. Observed: 308.1338.

EXAMPLE 6

Isopropyl 2R-Acetoxy-3S-carbamoyl-4-phenylbutanoate (VI, R=C$_6$H$_5$, R$^1$=CH$_3$)

Method A

To an ice cooled solution of the title product of the preceding Example (21.37 g, 0.0694 mol) in 100 ml of THF was added 9.68 ml (7.35 g, 0.0728 mol) of Et$_3$N followed by 6.93 ml (7.86 g, 0.0728 mol) of ClCOOEt. The mixture was stirred at 0° C. for 1.5 hours to assure complete conversion to the mixed anhydride of the formula (V) wherein R is C$_6$H$_5$, R$^1$ is CH$_3$ and R$^2$ is ethoxycarbonyl. Conc. NH$_4$OH (9.72 g) was added and the mixture stirred an additional 1.25 hours at 0°-5° C., then diluted with H$_2$O (200 ml) then extracted with EtOAc (2×200 ml). The combined EtOAc extracts were washed with 5% HCl (100 ml), dried over Na$_2$SO$_4$, filtered and evaporated under vacuum yield 16.6 g of present title product as a solid (78%). $^1$H-NMR delta 1.25 (3H, d, J=6), 1.27 (3H, d, J=6), 2.15 (3H, s), 2.8 (1H, m), 3.07 (2H, m), 5.01 (1H, d, J=4), 5.06 (1H, septet, J=6), 5.6-6.0 (2H, broad blob), 7.2 (5H, m). IR (CHCl$_3$) 3400, 3010, 1740, 1700 cm$^{-1}$. [alpha]$_D$= -15.6° (c=1.1, CHCl$_3$). Rf=0.50 (75% EtOAc/hexanes).

Elemental Analysis, Calc. for C$_{16}$H$_{21}$NO$_5$: C, 62.34, H, 6.79, N, 4.70. Found: C, 62.53, H, 6.89, N, 4.56.

Method B

Title product of the preceding Example (6.17 g, 0.020 mol) was dissolved in 40 mL of acetonitrile. N-Ethoxycarbonyl-2-ethoxy-1,2-dihydroquinoline (5.44 g, 0.022 mol) was added, followed by (NH$_4$)HCO$_3$ (4.75 g, 60 mmol). After stirring for 16 hours, the reaction mixture was diluted with 100 ml of ethyl acetate, washed 1×50 ml water and then 2×25 ml 5% HCl, dried over Na$_2$SO$_4$ and stripped to yield present title product, identified by $^1$H-NMR identical to the product of Method A.

EXAMPLE 7

Isopropyl 2R-Acetoxy-3S-(butoxycarbonylamino)-4-phenylbutanoate (VII, R=C$_6$H$_5$, R$^1$=CH$_3$)

To 8.26 g of the title product of the preceding Example (0.0268 mol) in 50 ml of t-BuOH was added 12.49 g (0.0282 mol) of Pb(OAc)$_4$. The reaction mixture was refluxed for 1 hour then allowed to cool to room temperature. 100 ml of EtOAc was added. The mixture was filtered then concentrated to give 9.60 g (94% yield) of title product as a dark yellow viscous oil. $^1$H-NMR delta 1.21 (3H, d, J=6), 1.22 (3H, d, J=6), 1.38 (9H, s), 2.23 (3H, s), 2.79 (1H, dd, J=6, 14), 2.93 (1H, dd, J=6,14), 4.50 (1H, br, q, J=7), 4.89 (1H, d, J=7), 5.92 (1H, d, J=2), 5.01 (1H, septet, J=6), 7.2 (5H, m). IR (neat) 3400, 3000, 1760-1700. [alpha]$_D$= -44.0° (c=1.1, CHCl$_3$). R$_f$=0.38 (25% EtOAc/hexanes). HRMS Calc. for C$_{20}$H$_{30}$NO$_6$ (M+1): 380.2065. Observed: 380.2073.

EXAMPLE 8

Isopropyl 3S-Amino-2R-hydroxy-4-phenylbutanoate (I, R=C$_6$H$_5$)

Anhydrous HCl was bubbled through a 0° C. solution of 5.84 g of title product of the preceding Example (0.0154 mol) in 50 ml of i-PrOH for 30 minutes. The reaction mixture was stirred at room temperature for 16 hours, then at 40° C. for 24 hours and finally refluxed for 8 hours. The i-PrOH was removed under vacuum and the residue dissolved in 50 ml of H$_2$O. This solution was extracted with EtOAc (50 ml) and the extracts discarded. The aqueous layer was made basic with 1N NaOH, then extracted with EtOAc (3×50 ml). The combined EtOAc extracts were dried over Na$_2$SO$_4$, filtered and evaporated in vacuum. A white solid was obtained which was recrystallized from diisopropyl ether to give 1.98 g (54%) of present title product as a white solid. Mp 109.9°-110.8° C. $^1$H-NMR delta 1.27 (3H, d, J=6), 1.28 (3H, d, J=6), 2.15 (3H, br s, exchangeable), 2.75 (1H, dd, J=8,14), 2.94 (1H, dd, J=5,14), 3.36 (1H, br m), 4.03 (1H, br s), 5.12 (1H, septet, J=6), 7.2 (5H, m). IR (CH$_2$Cl$_2$) 3500, 3000, 1720 cm$^{-1}$. [alpha]$_D$= -29.6° (c=1.0, CHCl$_3$) or -26.5° (c=1.4, MeOH). R$_f$=0.10 (75% EtOAc/hexanes).

EXAMPLE 9

Isopropyl 3S-Amino-4-cyclohexyl-2R-hydroxybutanoate (I, R=C$_6$H$_{11}$)

The shaking flask of a Paar hydrogenation apparatus was charged with 5 g of 5% Rh/C, 350 ml of isopropanol, 4.98 g of the title product of the preceding Example and 10 ml of concentrated HCl. The apparatus was pressurized to 50 psig with $H_2$ and hydrogenation allowed to proceed for 9 hours, by which time uptake of hydrogen had ceased. The catalyst was recovered by filtration over diatomaceous earth and washed 2×50 ml isopropanol. The combined filtrate and wash liquor was stripped to an oil, which was combined with 50 ml of $H_2O$, cooled to 0°–5° C., and the pH adjusted from 1.5 to 11.7 with about 1.2 ml of 50% NaOH. The resulting thick slurry was thinned by dilution with 50 ml of water, granulated for 1.5 hours and title product recovered by filtration, 3.1 g (61%); mp 80°–83° C.; $[alpha]_D$ −23.5° (c=1, $CH_3OH$); this product has been previously reported by Iizuka et al., loc. cit. and Hoover et al., loc. cit. in the form of the hydrochloride salt.

EXAMPLE 10

Diisopropyl 2R-Hydroxy-3S-(2-methyl-2propenyl)butanedioate

To 55.91 g (0.256 mol) of the title product of Example 1 in 300 ml of THF at −78° C. was added 379 ml (0.538 mol) of 1.42M lithium diisopropylamine (in hexanes) over a period of 30 minutes. The reaction mixture was stirred at −78° C. for 45 minutes, allowed to warm to −15° C., and held at that temperature for 1 hour. Methyallyl chloride (25.5 g, 0.282 moles) was added followed by 3.85 g (0.0256 moles) of NaI. The reaction mixture was stirred at −15° C. for 15 minutes, then allowed to warm to room temperature and stir for 18 hours, at which time 500 ml of water was added and the mixture was extracted with EtOAc (3×300 ml). The combined organic layers were washed with 100 ml of 5% HCl and then 100 ml of 5% NaOH, and dried over $Na_2SO_4$. After filtration and removal of the solvents under vacuum, 63 g of present title product was obtained as an orange oil. $^1$NMR delta 1.20 (6H, d, J=6), 1.28 (3H, d, J=6), 1.30 (3H, d, J=6), 1.78 (3H, s), 2.39 (1H, dd, J=9,16), 2.54 (1H, dd, J=5,16), 3.04 (1H, m), 3.19 (1H, d, J=7, —OH), 4.17 (1H, dd, J=5,9), 4.81 (2H, m), 4.98 (1H, septet, J=6), 5.09 (1H, septet, J=6). About 10% of the minor diastereomer can be observed at delta 4.36.

EXAMPLE 11

2R-Hydroxy-3S-(2-methyl-2-propenyl)butanedoic Acid

The entire product of the preceding Example was hydrolyzed by the method of Example 3, and 19.95 g of present title product isolated as a second orange oil. $^1$H NMR delta 1.58 (3H, s), 2.51 (2H, m), 3.25 (1H, m), 4.31 (1H, d, J=4), 4.85 (1H, br s), 4.89 (1H, br s). The minor diastereomer appears in the product at delta 4.51 (1H, d, J=5). IR (neat) 3450–2600, 1750 $cm^{-1}$. $[alpha]_D$=−5.16° (c=1.8, $CHCl_3$). HRMS Calculated for $C_7H_9O_5$ (P-Me): 173.0447. Observed: 173.0468.

EXAMPLE 12

2R-Hydroxy-3S-(2-methylpropyl)butanedioic Acid (II, R=$(CH_3)_2CH$)

Title product of the preceding Example, 18.20 g (0.0968 mol) was dissolved in 200 ml of MeOH. Then 2.68 g (0.0029 mol) of $(Ph_3P)_3RhCl$ was added. The hydrogenation was carried out for 24 hours at 30 psig. The MeOH was removed under vacuum. The residue was dissolved in EtOAc and filtered through 100 g of silica gel. After evaporation of the solvent, 15.53 g of present title product was obtained as an oil (83% yield). $^1$H-NMR 0.93 (3H, d, J=6), 0.95 (3H, d, J=6), 1.55–1.85 (3H, m), 3.09 (1H, m), 4.29 (1H, d, J=5). IR (neat) 3450–2600, 1750 $cm^{-1}$. $[alpha]_D$=+8.7° (c=1.4, $CHCl_3$), HRMS Calculated for $C_8H_{15}O_5$ (P+1): 191.0915. Observed 191.0920.

EXAMPLE 13

Isopropyl 2R-Acetoxy-3-carboxy-5-methylhexanoate (IV, R=$(CH_3)_2CH$, $R^1$=$CH_3$)

To 100 ml of acetyl chloride was added 15.33 g of title product of the preceding Example. The reaction mixture was stirred at room temperature for 16 hours. The excess acetyl chloride and acetic acid were removed by distillation first at 1 atm and then under vacuum. To the resulting cyclic anhydride was added 100 ml of i-PrOH and the mixture stirred at room temperature for 5 hours. The excess i-PrOH was removed under vacuum. The last traces of i-PrOH were removed by azeotroping with toluene. 14.14 g of a clear, colorless liquid was obtained (64% yield). $^1$H NMR delta 0.90 (6H, m), 1.19 (3H, d, J=6), 1.21 (3H, d, J=6), 1.4 (1H, m), 1.5–1.8 (2H, m), 2.15 (3H, s), 3.06 (1H, m), 5.07 (1H, septet, J=6), 5.11 (1H, d, J=5). IR (neat) 3300–2600, 1760–1700 $[alpha]_D$=+8.7° (c=1.4, $CHCl_3$). HRMS Calculated for $C_{13}H_{23}O_6$ (P+1): 275.1488. Observed: 275.1452.

EXAMPLE 14

Isopropyl 2R-Acetoxy-3S-carbamoyl-5-methylhexanoate (VI, R=$(CH_3)_2CH$, R=$CH_3$)

By Method A of Example 6, the title product of the preceding Example (5.60 g, 0.0204 mol) was converted to 3.90 g of present title product (70% yield) as a dark oil. $^1$H NMR delta 0.90 (3H, d, J=6), 0.92 (3H, d, J=6), 1.8 (6H, m), 1.5–1.9 (3H, m), 2.15 (3H, s), 2.86 (1H, m), 5.02 (1H, d, J=6), 5.07 (1H, septet, J=6), 5.58 (1H, br s), 5.82 (1H, br s). IR (neat) 3400, 3010, 1740, 1690 $cm^{-1}$. $[alpha]_D$=+4.31° (c=1.2, $CHCl_3$). HRMS Calculated for $C_{13}H_{24}NO_5$ (P+1): 274.1648. Found: 274.1599.

EXAMPLE 15

Iropropyl 2R-Acetoxy-3S-(t-butoxycarbonylamino)-5-methylhexanoate (VII, R=$(CH_3)_2CH$, $R^1$=$CH_3$)

By the method of Example 7, title product of the preceding Example (3.00 g, 0.0109 mol) was converted to 2.43 g (67%) of present title product as a dark yellow viscous oil. $^1$H-NMR delta 0.92 (3H, d, J=6), 0.96 (3H, d, J=6), 1.28 (3H, d, J=6), 1.30 (3H, d, J=6), 1.42 (9H, s), 2.19 (3H, s), 4.32 (1H, br q, J=5), 4.69 (1H, br d, J=7), 5.00 (1H, d, J=2), 5.01 (1H, septet, J=6). IR (neat) 3400, 3000, 1750, 1720. $[alpha]_D$=−25.8° (c=0.97, $CHCl_3$). HRMS Calculated for $C_{17}H_{32}NO_6$ (P+1): 346.2221. Observed 346.2242.

EXAMPLE 16

Isopropyl 3S-Amino-2R-hydroxy-5-methylhexanoate Hydrochloride (I, R=$(CH_3)_2CH$, HCl Salt)

Title product of the preceding Example (1.07 g, 0.0031 mol) was added to 50 ml i-PrOH. Gaseous HCl was passed into the solution until 5 g had been absorbed. The reaction mixture was refluxed for 18 hours. The i-PrOH was removed under vacuum yielding 0.74 g (100%) of present title product as a white powder. The spectral characteristics were the same as those previously reported (U.S. Pat. No. 4,656,269).

EXAMPLE 17

3S-(Cyclohexylmethyl)-2R-hydroxybutanedioic Acid (II, R=C₆H₁₁)

Title product of Example 3 (5.0 g, 22.3 mmol) in 50 ml CH₃OH was hydrogenated over 5% Rh/Al₂O₃ (2.0 g) at 50 psig for 16 hours. Catalyst was recovered according to Example 9, and 5.1 g of crude product recovered by stripping mother liquors to dryness. Purified title product (4.0 g) was obtained by recrystallization from CH₂Cl₂; mp 125°-128° C.; ¹H-NMR (CD₃COOD) delta (ppm) 3.11 (dt, J=4.3, 7.4, 1H), 4.41 (d, J=4.3, 1H), 11.5 (broad s).

EXAMPLE 18

2R-Acetoxy-3S-(cyclohexylmethyl)butanedioic Anhydride (III, R=C₆H₁₁, R¹=CH₃)

By the method of Example 4, title product of the preceding Example (5.76 g) was converted to present title product. The entire product was used directly in the next step.

EXAMPLE 19

Isopropyl 2R-Acetoxy-3S-carboxy-4-cyclohexylbutanoate (IV, R=C₆R₁₁, R¹=CH₃)

By the method of Example 5, the entire product of the preceding Example was converted to present title product, 8.90 g, as clear, colorless oil (contaminated with some toluene); ¹H-NMR delta 1.23 (d, J=6.6, 3H), 1.25 (d, J=6.5, 3H), 2.14 (s, 3H), 3.11 (m, 1H), 5.06 (septet, J=6.6, 1H), 5.18 (d, J=5.44, 1H).

EXAMPLE 20

Isopropyl 2R-Acetoxy-3S-carbamoyl-4-cyclohexylbutanoate (VI, R=C₆H₁₁, R¹=CH₃)

By Method B of Example 6, the entire batch of product of the preceding Example (0.025 mmol) was converted to present title product 7.78 g, as a viscous oil; ¹H-NMR delta 1.24 (d, J=6.5, 3H), 1.26 (d, J=6.5, 3H), 2.13 (s, 3H), 2.90 (m, 1H), 5.0 (d, J=6.7, 1H), 5.06 (septet, J=6.5, 1H), 5.4 (br s, 1H), 5.6 (br s, 1H).

The same product is obtained via the mixed anhydride (V, R=C₆H₁₁, R¹=CH₃, R²=ethoxycarbonyl) according to method A of Example 6.

EXAMPLE 21

Isopropyl 2R-Acetoxy-3S-(t-butoxycarbonylamino)-4-cyclohexylbutanoate (VII, R=C₆H₁₁, R¹=CH₃)

By the method of Example 7, title product of the preceding Example (3.13 g, 0.010 mol) was converted to present title product, 3.06 g as a viscous oil; ¹H-NMR delta 1.23 (d, J=6, 3H), 1.25 (d, J=6, 3H), 1.38 (s, 9H), 2.17 (s, 3H), 4.35 (m, 1H), 4.68 (d, J=7, 1H), 4.97 (d, J=2, 1H), 5.01 (septet, J=6, 1H).

EXAMPLE 22

Isopropyl 3S-Amino-4-cyclohexyl-2R-hydroxybutanoate (I, R=C₆H₁₁)

Title product of the preceding Example (3.00 g, 0.0078 mol) was dissolved in 75 ml of isopropanol. Methanesulfonic acid (2 ml) was added and the mixture refluxed for 48 hours. The solvent was stripped in vacuo, and the residue taken up in 50 ml of water and with vigorous stirring slowly made basic with 15% NaOH. Title product, 0.79 g, recovered by filtration, was identical with the product of Example 9.

I claim:

1. A step-wise process for the preparation of an isopropyl 3S-amino-2R-hydroxyalkanoate of the formula

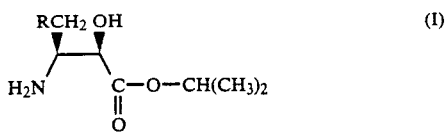

wherein R is phenyl, isopropyl or cyclohexyl, which comprises the steps of (a) reacting a 2R,3S-malic acid derivative of the formula

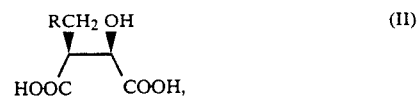

with excess of an acid chloride of the formula R¹COCl or an anhydride of the formula (R¹CO)₂O, wherein R¹ is (C₁-C₄)alkyl or phenyl, to form a cyclic anhydride of the formula

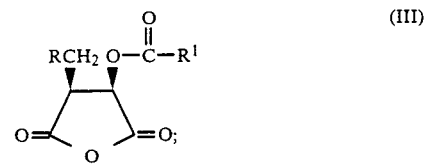

(b) reacting said cyclic anhydride of the formula (III) with excess of isopropanol to form a hemiester of the formula

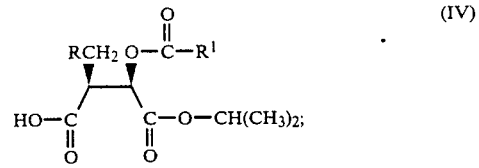

(c) activating the carboxylic acid group of said hemiester of the formula (IV) and reacting the resulting activated form of the acid with NH₃ to form an ester-amide of the formula

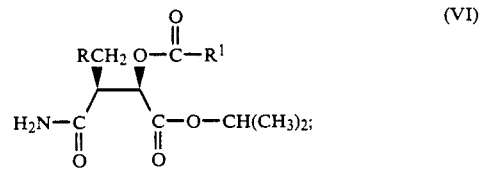

(d) rearranging said ester-amide of the formula (VI) by the action of Pb(OCOCH₃)₄ in t-butanol to form a t-butyloxycarbonylamino ester of the formula

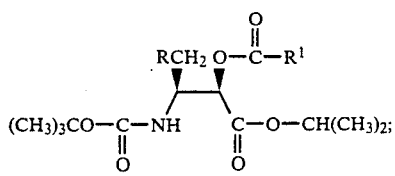

(e) solvilizing said t-butyloxycarbonylamino ester of the formula (VII) with isopropanol in the presence of an acid catalyst to form said isopropyl 3S-amino-2R-hydroxyalkanoate of the formula (I).

2. A process of claim 1 wherein $R^1$ is methyl.

3. A process of claim 1 wherein the carboxylic acid group of said hemiester of the formula (IV) is activated in the form of a mixed anhydride of the formula wherein $R^2$ is $(C_2-C_4)$alkoxycarbonyl, phenoxycarbonyl or benzyloxycarbonyl.

4. A process of claim 3 wherein $R^1$ is methyl.

5. A process of claim 3 wherein $R^2$ is ethoxycarbonyl.

6. A process of claim 1 wherein R is phenyl which further comprises hydrogenation of the isopropyl 3S-amino-2R-hydroxy-4-phenylbutyrate of the formula (I) wherein R is phenyl over a rhodium catalyst to form isopropyl 3S-amino-4-cyclohexyl-2R-hydroxybutyrate of the formula (I) wherein R us cyclohexyl.

* * * * *

UNITED STATES PATENT AND TRADEMARK OFFICE
CERTIFICATE OF CORRECTION

PATENT NO. : 5,036,155
DATED : July 30, 1991
INVENTOR(S) : Robert W. Dugger

It is certified that error appears in the above-identified patent and that said Letters Patent is hereby corrected as shown below:

Column 10, line 17 - "2R-Acetoxy-3S-(butoxycarbonylamino)-4-phenylbutanoate" should read -- 2R-Acetoxy-3S-(t-butoxycarbonylamino)-4-phenylbutanoate--.

Column 11, line 44 - "2R-Hydroxy-3S-(2-methyl-2-propenyl)-butanedoic Acid" should read -- 2R-Hydroxy-3S-(2-methyl-2-propenyl)-butanedioic Acid--.

Column 12, lines 29, 30 - "(VI, R = $(CH_3)_2CH$, R = $CH_3$)" should read -- (VI, R = $(CH_3)_2CH$, $R^1$ = $CH_3$) --.

Column 15, line 2 - "solvilizing" should read -- solvolizing --.

Column 16, line 19 - "us" should read -- is --.

Signed and Sealed this

Sixth Day of July, 1993

Attest:

MICHAEL K. KIRK

Attesting Officer

Acting Commissioner of Patents and Trademarks